United States Patent
Dobak, III

(10) Patent No.: US 7,063,718 B2
(45) Date of Patent: Jun. 20, 2006

(54) SELECTIVE ORGAN HYPOTHERMIA METHOD AND APPARATUS

(75) Inventor: John D. Dobak, III, La Jolla, CA (US)

(73) Assignee: Innercool Therapies, Inc., San Diego, CA (US)

(*) Notice: Subject to any disclaimer, the term of this patent is extended or adjusted under 35 U.S.C. 154(b) by 0 days.

(21) Appl. No.: 10/382,223

(22) Filed: Mar. 5, 2003

(65) Prior Publication Data

US 2003/0144714 A1 Jul. 31, 2003

Related U.S. Application Data

(60) Continuation of application No. 09/834,054, filed on Apr. 12, 2001, now Pat. No. 6,558,412, which is a continuation of application No. 09/650,940, filed on Aug. 30, 2000, now Pat. No. 6,482,226, which is a continuation of application No. 09/306,866, filed on May 7, 1999, now Pat. No. 6,235,048, which is a division of application No. 09/012,287, filed on Jan. 23, 1998, now Pat. No. 6,051,019.

(51) Int. Cl.
*A61F 7/00* (2006.01)

(52) U.S. Cl. .................. 607/105; 607/106; 607/113

(58) Field of Classification Search ............... 607/96, 607/104–106, 113
See application file for complete search history.

(56) References Cited

U.S. PATENT DOCUMENTS

| | | | |
|---|---|---|---|
| 2,308,484 A | 1/1943 | Auzin et al. | |
| 2,374,609 A | 4/1945 | McCollum | |
| 2,615,686 A | 10/1952 | Davidson | |
| 2,672,032 A | 3/1954 | Towse | |
| 2,913,009 A | 11/1959 | Kuthe | |
| 3,125,096 A | 3/1964 | Antiles et al. | |
| 3,298,371 A | 1/1967 | Lee | |
| 3,425,419 A * | 2/1969 | Dato | ............ 607/106 |
| 3,504,674 A | 4/1970 | Swenson et al. | |
| 3,612,175 A | 10/1971 | Ford et al. | |
| 3,674,031 A | 7/1972 | Weiche | |
| 3,696,813 A | 10/1972 | Wallach | |
| 3,865,116 A | 2/1975 | Brooks | |
| 3,888,259 A | 6/1975 | Miley | |
| 3,971,383 A | 7/1976 | Van Gerven | |
| 4,038,519 A | 7/1977 | Foucras | |

(Continued)

FOREIGN PATENT DOCUMENTS

AU 730835 B2 1/1997

(Continued)

OTHER PUBLICATIONS

Gorman-Rupp; Hypothermia Machine (Jul.-Aug. 1972).

(Continued)

*Primary Examiner*—Roy D. Gibson
(74) *Attorney, Agent, or Firm*—Mayor & Williams PC; Mark D. Wieczorek, Esq.; Karin L. Williams, Esq.

(57) ABSTRACT

A method and apparatus for performing hypothermia of a selected organ without significant effect on surrounding organs or other tissues. A flexible catheter is inserted through the vascular system of a patient to place the distal tip of the catheter in an artery feeding the selected organ. A compressed refrigerant is pumped through the catheter to an expansion element near the distal tip of the catheter, where the refrigerant vaporizes and expands to cool a flexible heat transfer element in the distal tip of the catheter. The heat transfer element cools the blood flowing through the artery, to cool the selected organ, distal to the tip of the catheter.

5 Claims, 3 Drawing Sheets

U.S. PATENT DOCUMENTS

| | | |
|---|---|---|
| 4,153,048 A | 5/1979 | Magrini |
| 4,190,033 A | 2/1980 | Foti |
| 4,231,425 A | 11/1980 | Engstrom |
| 4,275,734 A | 6/1981 | Mitchiner |
| 4,298,006 A | 11/1981 | Parks |
| 4,318,722 A | 3/1982 | Altman |
| 4,323,071 A | 4/1982 | Simpson et al. |
| 4,427,009 A | 1/1984 | Wells et al. |
| 4,445,500 A | 5/1984 | Osterholm |
| 4,483,341 A | 11/1984 | Witteles |
| 4,497,890 A | 2/1985 | Helbert |
| 4,502,286 A | 3/1985 | Okada et al. |
| 4,569,355 A | 2/1986 | Bitterly |
| 4,581,017 A | 4/1986 | Sahota |
| 4,602,642 A | 7/1986 | O'Hara et al. |
| 4,655,746 A | 4/1987 | Daniels et al. |
| 4,672,962 A | 6/1987 | Hershenson |
| 4,745,922 A | 5/1988 | Taylor |
| 4,748,979 A | 6/1988 | Hershenson |
| 4,750,493 A | 6/1988 | Brader |
| 4,762,129 A | 8/1988 | Bonzel |
| 4,762,130 A | 8/1988 | Fogarty et al. |
| 4,781,799 A | 11/1988 | Herbert, Jr. et al. |
| 4,820,349 A | 4/1989 | Saab |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,920,963 A | 5/1990 | Brader |
| 4,951,677 A | 8/1990 | Crowley et al. |
| 4,964,409 A | 10/1990 | Tremulis |
| 4,973,493 A | 11/1990 | Guire |
| 4,979,959 A | 12/1990 | Guire |
| 5,000,734 A | 3/1991 | Boussignac et al. |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishwara et al. |
| 5,108,390 A | 4/1992 | Potocky et al. |
| RE33,911 E | 5/1992 | Samson et al. |
| 5,110,721 A | 5/1992 | Anaise et al. |
| 5,112,438 A | 5/1992 | Bowers |
| 5,117,822 A | 6/1992 | Laghi |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,180,364 A | 1/1993 | Ginsburg |
| 5,190,539 A | 3/1993 | Fletcher et al. |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,241,951 A | 9/1993 | Mason et al. |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,281,213 A | 1/1994 | Milder et al. |
| 5,281,215 A | 1/1994 | Milder |
| 5,306,261 A | 4/1994 | Alliger et al. |
| 5,310,440 A | 5/1994 | Zingher |
| 5,322,514 A | 6/1994 | Steube et al. |
| 5,322,515 A | 6/1994 | Karas et al. |
| 5,322,518 A | 6/1994 | Schneider et al. |
| 5,330,435 A | 7/1994 | Vaillancourt |
| 5,330,438 A | 7/1994 | Gollobin et al. |
| 5,334,193 A | 8/1994 | Nardella |
| 5,340,290 A | 8/1994 | Clemens |
| 5,342,181 A | 8/1994 | Schock et al. |
| 5,342,301 A | 8/1994 | Saab |
| 5,344,436 A | 9/1994 | Fontenot et al. |
| 5,354,186 A | 10/1994 | Murtuza et al. |
| 5,365,750 A | 11/1994 | Greenthal |
| 5,368,591 A | 11/1994 | Lennox et al. |
| 5,383,854 A | 1/1995 | Safar et al. |
| 5,383,918 A | 1/1995 | Panetta |
| 5,395,314 A | 3/1995 | Klatz et al. |
| 5,395,331 A | 3/1995 | O'Neil et al. |
| 5,403,281 A | 4/1995 | O'Neill et al. |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,673 A | 8/1995 | Baust et al. |
| 5,443,456 A | 8/1995 | Alliger et al. |
| 5,462,521 A | 10/1995 | Brucker et al. |
| 5,486,204 A | 1/1996 | Clifton |
| 5,486,208 A | 1/1996 | Ginsburg |
| 5,496,271 A | 3/1996 | Burton et al. |
| 5,531,776 A | 7/1996 | Ward et al. |
| 5,549,559 A | 8/1996 | Eshel |
| 5,554,119 A | 9/1996 | Harrison et al. |
| 5,558,644 A | 9/1996 | Boyd et al. |
| 5,573,532 A | 11/1996 | Chang et al. |
| 5,578,008 A | 11/1996 | Hara |
| 5,584,804 A | 12/1996 | Klatz et al. |
| 5,588,438 A | 12/1996 | McKown et al. |
| 5,591,162 A | 1/1997 | Fletcher et al. |
| 5,620,480 A | 4/1997 | Rudie |
| 5,622,182 A | 4/1997 | Jaffe |
| 5,624,392 A | 4/1997 | Saab |
| 5,630,837 A | 5/1997 | Crowley |
| 5,643,197 A | 7/1997 | Brucker et al. |
| 5,647,051 A | 7/1997 | Neer |
| 5,653,692 A | 8/1997 | Masterson et al. |
| 5,709,654 A | 1/1998 | Klatz et al. |
| 5,713,941 A | 2/1998 | Robins et al. |
| 5,716,386 A | 2/1998 | Ward et al. |
| 5,733,318 A | 3/1998 | Augustine |
| 5,735,809 A | 4/1998 | Gorsuch |
| 5,787,715 A | 8/1998 | Dobak, III et al. |
| 5,797,878 A | 8/1998 | Bleam |
| 5,799,661 A | 9/1998 | Boyd et al. |
| 5,800,480 A | 9/1998 | Augustine et al. |
| 5,800,483 A | 9/1998 | Vought |
| 5,800,516 A | 9/1998 | Fine et al. |
| 5,807,391 A | 9/1998 | Wijkamp |
| 5,820,593 A | 10/1998 | Safar et al. |
| 5,824,030 A | 10/1998 | Yang et al. |
| 5,827,222 A | 10/1998 | Klatz et al. |
| 5,827,237 A | 10/1998 | Macoviak et al. |
| 5,827,269 A | 10/1998 | Saadat |
| 5,833,671 A | 11/1998 | Macoviak et al. |
| 5,837,003 A * | 11/1998 | Ginsburg .................... 607/106 |
| 5,861,021 A | 1/1999 | Thome et al. |
| 5,868,735 A | 2/1999 | Lafontaine |
| 5,871,526 A | 2/1999 | Gibbs et al. |
| 5,873,835 A | 2/1999 | Hastings et al. |
| 5,879,316 A | 3/1999 | Safar et al. |
| 5,879,329 A | 3/1999 | Ginsburg |
| 5,899,898 A | 5/1999 | Arless et al. |
| 5,899,899 A | 5/1999 | Arless et al. |

| | | | |
|---|---|---|---|
| 5,901,783 A | 5/1999 | Dobak, III et al. | |
| 5,902,268 A | 5/1999 | Saab | |
| 5,906,588 A | 5/1999 | Safar et al. | |
| 5,906,594 A | 5/1999 | Scarfone et al. | |
| 5,906,636 A | 5/1999 | Casscells, III et al. | |
| 5,913,856 A | 6/1999 | Chia et al. | |
| 5,913,885 A | 6/1999 | Klatz et al. | |
| 5,913,886 A | 6/1999 | Soloman | |
| 5,916,242 A | 6/1999 | Schwartz | |
| 5,957,963 A | 9/1999 | Dobak, III | |
| 5,971,979 A | 10/1999 | Joye et al. | |
| 5,989,238 A | 11/1999 | Ginsburg | |
| 6,007,692 A | 12/1999 | Herbert et al. | |
| 6,019,783 A | 2/2000 | Philips et al. | |
| 6,022,336 A | 2/2000 | Zadno-Azizi et al. | |
| 6,024,740 A | 2/2000 | Lesh et al. | |
| 6,033,383 A * | 3/2000 | Ginsburg | 604/113 |
| 6,042,559 A | 3/2000 | Dobak, III | |
| 6,051,019 A | 4/2000 | Dobak, III | |
| 6,096,068 A | 8/2000 | Dobak, III et al. | |
| 6,110,168 A | 8/2000 | Ginsburg | |
| 6,126,684 A | 10/2000 | Gobin et al. | |
| 6,146,184 A | 11/2000 | Wilson et al. | |
| 6,146,411 A | 11/2000 | Noda et al. | |
| 6,149,670 A | 11/2000 | Worthen et al. | |
| 6,149,673 A | 11/2000 | Ginsburg | |
| 6,149,676 A | 11/2000 | Ginsburg | |
| 6,149,677 A | 11/2000 | Dobak, III | |
| 6,165,207 A | 12/2000 | Balding et al. | |
| 6,235,048 B1 | 5/2001 | Dobak, III | |
| 6,306,161 B1 | 10/2001 | Ginsburg | |
| 6,315,995 B1 | 11/2001 | Pinsky et al. | |
| 6,316,403 B1 | 11/2001 | Pinsky et al. | |
| 6,354,099 B1 | 3/2002 | Bieberich | |
| 6,405,080 B1 | 6/2002 | Lasersohn et al. | |
| 6,432,124 B1 | 8/2002 | Worthen et al. | |
| 6,436,131 B1 | 8/2002 | Ginsburg | |
| 6,451,045 B1 | 9/2002 | Walker et al. | |
| 6,527,798 B1 | 3/2003 | Ginsburg et al. | |
| 2001/0005791 A1 | 6/2001 | Ginsburg et al. | |
| 2001/0016764 A1 | 8/2001 | Dobak, III | |
| 2001/0047196 A1 | 11/2001 | Ginsburg et al. | |
| 2001/0049545 A1 | 12/2001 | Lasersohn et al. | |
| 2002/0029073 A1 | 3/2002 | Schwartz | |
| 2002/0045852 A1 | 4/2002 | Saab | |
| 2002/0045925 A1 | 4/2002 | Keller et al. | |
| 2002/0111616 A1 | 8/2002 | Dae et al. | |
| 2002/0111657 A1 | 8/2002 | Dae et al. | |
| 2002/0156421 A1 | 10/2002 | Noda et al. | |

FOREIGN PATENT DOCUMENTS

| | | |
|---|---|---|
| AU | 739996 B2 | 1/1999 |
| AU | 743945 B2 | 2/2002 |
| EP | 0655225 A1 | 5/1993 |
| EP | 0 664 990 | 11/1997 |
| FR | 2 447 406 | 3/1980 |
| SU | 806 029 | 2/1981 |
| WO | WO 91/05528 | 5/1991 |
| WO | WO 93/04727 | 3/1993 |
| WO | WO 95/01814 | 1/1995 |
| WO | WO 96/40347 | 12/1996 |
| WO | WO 97/01374 | 1/1997 |
| WO | WO 97/25011 | 7/1997 |
| WO | WO 98/26831 | 6/1998 |
| WO | WO 98/31312 | 7/1998 |
| WO | WO 99/04211 | 1/1999 |
| WO | WO 99/37226 | 7/1999 |
| WO | WO 99/48449 | 9/1999 |
| WO | WO 99/66970 | 12/1999 |
| WO | WO 99/66971 | 12/1999 |
| WO | WO 00/09054 | 2/2000 |
| WO | WO 00/10494 | 3/2000 |
| WO | WO 00/38601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 | 1/2001 |
| WO | WO 01/08580 | 2/2001 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13809 | 3/2001 |
| WO | WO 01/13837 | 3/2001 |
| WO | WO 01/17471 | 3/2001 |
| WO | WO 01/19447 | 3/2001 |
| WO | WO 02/13710 | 2/2002 |
| WO | WO 02/19934 | 3/2002 |
| WO | WO 02/26175 | 4/2002 |
| WO | WO 02/26176 | 4/2002 |
| WO | WO 02/36180 | 5/2002 |
| WO | WO 02/43577 | 6/2002 |

OTHER PUBLICATIONS

Gorman-Rupp; Hypothermia Machine (Apr. 1972).

Ambrus; *The Biphasic Nature and Temperature Dependence of the Activation of Human Plasminogen by Urokinase*; May 1979; pp. 339-347; Research Communications in Chemical Pathology and Pharmacology, vol. 24, No. 2.

Bigelo; *Hypothermia, Its Possible Role in Cardiac Surgery*; Nov. 1959; pp. 849-866; Annals of Surgery, vol. 132, No. 5.

Cheatle; *Cryostripping the Long and Short Saphenous Veins*; Jan. 1993; one page; Br. J. Surg., vol. 80.

Dexter; *Blood Warms as It Blows Retrograde from a Femoral Cannulation Site to the Carotid Artery During Cardiopulmonary Bypass*; Nov. 1994; pp. 393-397; Perfusion, vol. 9, No. 6.

Gillinov; *Superior Cerebral Protection with Profound Hypothermia During Circulatory Arrest*; Nov. 1992; pp. 1432-1439; Ann. Thorac. Surg., vol. 55.

Higazi; *The Effect of Ultrasonic Irradiation and Temperature on Fibrinolytic Activity in Vitro*; Aug. 1992; p. 251-253; Thrombosis Research, vol. 69, No. 2.

Imamaki; "*Retrograde Cerebral Perfusion with Hypothermic Blood Provides Efficient Protection of the Brain*"; Jul. 1995; pp. 325-333; Journal of Cardiac Surgery, vol. 10, No. 4, Part 1.

Jolin; *Management of a Giant Intracranial Aneurysm Using Surface-Heparinized Extracorporeal Circulation and Controlled Deep Hypothermic Low Flow Perfusion*; Aug. 1992; pp. 756-760; Acta Anaesthesiologica Scandinavia.

Jos R.C. Jansen, Ph.D., et al. (1997) *Near continuous cardiac output by thermodilution*. Journal of Clinical Monitoring 13:233-239.

Kimoto; *Open Heart Surgery under Direct Vision with the Aid of Brain-Cooling by Irrigation*; Jul. 1955; pp. 592-603; Surgery, vol. 39, No. 4.

Marekovic, Z.; *Abstract of Renal Hypothermia in Situ by Venous Passages: Experimental Work on Dogs*; 1980; Eur Urol 6(2); 1 page.

Meden; *Effect of Hypothermia and Delayed Thrombolysis in a Rat Embolic Stroke Model*; Dec. 1993; pp. 91-98; Acta Neurologica Scandinavica.

Meden; *The Influence of Body Temperature on Infarct Volume and Thrombolytic Therapy in a Rat Embolic Stroke Model*; Feb. 1994; pp. 131-138; Brain Research, vol. 647.

Milleret, Rene; *La cryo-chirurgie danes les varices des mimbres inferieurs*; Angiologie; Supplement au No. 110.

Milleret; Abstract of *Cryosclerosis of the Saphenous Veins in Varicose Reflux in the Obese and Elderly*; Oct. 1981; one page; Phlebologie, vol. 34, No. 4.

Parkins; Brain Cooling in the Prevention of Brain Damage During Periods of Circulatory Occlusion in Dogs; Apr. 1954; pp. 284-289; Annals of Surgery, vol. 140, No. 3.

Piepgras; *Rapid Active Internal Core Cooling for Induction of Moderate Hypothermia in Head Injury by Use of an Extracorporeal Heat Exchanger*, Feb. 1998; pp. 311-318; Neurosurgery, vol. 42, No. 2.

Rijken; *Plasminogen Activation at Low Temperatures in Plasma Samples Containing Therapeutic Concentrations of Tissue-Type Plasminogen Activator or Other Thrombolytic Agents*; Oct. 1989; pp. 47-52; place of publication unknown.

Schwartz, A.E. et al.; (1996); *Isolated cerebral hypothermia by single carotid artery perfusion of extracorporeally cooled blood in baboons*; Neurosurgery 39(3):577-582.

Schwartz; *Cerebral Blood Flow during Low-flow Hypothermic Cardiopulmonary Bypass in Baboons*; Jun. 1994; pp. 959-964; Anesthesiology, vol. 81, No. 4.

Schwartz; *Selective Cerebral Hypothermia by Means of Transfemoral Internal Carotid Artery Catheterization*; May 1996; pp. 571-572; Radiology, vol. 201, No. 2.

Steen; *The Detrimental Effects of Prolonged Hypothermia and Rewarming in the Dog*; Aug. 1979; pp. 224-230; Anesthesiology, vol. 52, No. 3.

Vandam; *Hypothermia*; Sep. 1959; pp. 546-553; The New England Journal of Medicine.

White; *Cerebral Hypothermia and Circulatory Arrest*; Jul. 1978; pp. 450-458; Mayo Clinic Proceedings, vol. 53.

Yenari; *Thrombolysis with Tissue Plasminogen Activator (TPA) is Temperature Dependent*; Jul. 1994; pp. 475-481; Thrombosis Research, vol. 77, No. 5.

Yoshihara; *Changes in Coagulation and Fibrinolysis Occurring in Dogs during Hypothermia*; Aug. 1984; pp. 503-512; Thrombosis Research, vol. 37, No. 4.

Zarins; *Circulation in Profound Hypothermia*; Nov. 1972; pp. 97-104; Journal of Surgical Research, vol. 14, N. 2.

Benzinger, T. H. "On Physical Heat Regulation and the Sense of Temperature in Man," *Proc. N.A.S.* 45:645-650 (1959).

Cabanac, M. "Selective Brain Cooling and thermoregulatory Set-Point," *Journ. of Basic & Clinical Phsysiol. & Pharmacology* 9 (1):3-13 (1998).

Cabanac, M. "Selective Brain Cooling in Humans : 'Fancy' or Fact?" *Point-Counterpoint* 7:1143-1147 (Sep. 1993).

Colvett, Kyle, A. F. Althausen, B. Bassil, N. M. Heney, F. V. McGovern, H. H. Young, D. S. Kaufman, A. L. Zietman, and W. U. Shipley, "Opportunities with Combined Modality Therapy for Selective Organ Preservation in Muscle-Invasive Bladder Cancer," *Journ. of Surg. Oncology* 63:201-208 (1996).

Jessen, C., J. B. Mercer, and S. Puschmann "Intravascular Heat Exchanger for Conscious Goats," *Pflügers Arch*. 268-265 (1977).

Maas, C., R. Kok, P. Segers, A. Boogaart, S. Eilander, I. de Vries, "Intermittent Antegrade/Selective Cerebral Perfusion During Circulatory Arrest for Repair of the Aortic Arch," *Perfusion* 12:127-132 (1997).

Mercer, J. B. and C. Jessen, "Effects of Total Body Core Cooling on Heat Production of Conscious Goats," *Pflügers Arch*. 373:259-267 (1978).

Schubert, A. "Side Effects of Mild Hypothermia," *Journ. of Neurosurgical Anesthesiology*, 7(2):139-147 (1995).

Hederer, G., et al.; "Animal Experiment Observations Regarding Cardiac Surgery under Intravascular Hypothermia"; Labgebbecjs Arch. U. Dtsch. A. Chir., Bd. 283, S. 601-625 (1957) (German article with English translation).

Behmann, F.W; "Heat Generation Control during Artificial Hypothermia: II. Theoretical Examinations"; Pflügers Archiv, Bd. 266, S. 422-446 (1958) (German article with English translation).

Behmann, F.W., et al.; "Heat Generation Control during Artificial Hypothermia: I: Experimental Examination of the Influence of Anesthetic Depth"; Pflügers Archiv, Bd, 266, S. 408-421 (1958) (German article with English translation).

Behmann, F.W., et al.; Intravascular Cooling, a Method to Achieve Controllable Hypothermia; Pflügers Archive, vol. 263, pp. 145-165 (1956) (German article with English translation).

Behmann, F.W.; "Heat Generation Control during Artificial Hypothermia, an article about the economic problem of trembling stages"; Pflügers Archive, vol. 263, pp. 166-187 (1956) (German article with English translation).

Behmann, F.W.; "Regulation of heat production in experimental hypothermia of homothermal animals"; Naunyn Schmiedebergs Arch Exp Pathol Pharmakol; 228 (1-2): 126-128 (1956). (German article with English translation).

* cited by examiner

SELECTIVE ORGAN HYPOTHERMIA METHOD AND APPARATUS

CROSS REFERENCE TO RELATED APPLICATIONS

This application is a continuation application of U.S. application Ser. No. 09/834,054, filed Apr. 12, 2001, titled "Selective Organ Hypothermia Method and Apparatus" now U.S. Pat. No. 6,558,412, which is a continuation application of U.S. application Ser. No. 09/650,940, filed Aug. 30, 2000, titled "Selective Organ Hypothermia Method and Apparatus", now U.S. Pat. No. 6,482,226, which is a continuation of U.S. application Ser. No. 09/306,866, filed May 07, 1999, titled "Selective Organ Hypothermia Method and Apparatus", now U.S. Pat. No. 6,235,048, which is a divisional application of U.S. application Ser. No. 09/012,287, filed Jan. 23, 1998, titled "Selective Organ Hypothermia Method and Apparatus", now U.S. Pat. No. 6,051,019.

STATEMENT REGARDING FEDERALLY SPONSORED RESEARCH OR DEVELOPMENT

Not Applicable

BACKGROUND OF THE INVENTION

1. Field of the Invention

The current invention relates to selective cooling, or hypothermia, of an organ, such as the brain, by cooling the blood flowing into the organ. This cooling can protect the tissue from injury caused by anoxia or trauma.

2. Background Information

Organs of the human body, such as the brain, kidney, and heart, are maintained at a constant temperature of approximately 37° C. Cooling of organs below 35° C. is known to provide cellular protection from anoxic damage caused by a disruption of blood supply, or by trauma. Cooling can also reduce swelling associated with these injuries.

Hypothermia is currently utilized in medicine and is sometimes performed to protect the brain from injury. Cooling of the brain is generally accomplished through whole body cooling to create a condition of total body hypothermia in the range of 20° to 30° C. This cooling is accomplished by immersing the patient in ice, by using cooling blankets, or by cooling the blood flowing externally through a cardiopulmonary bypass machine. U.S. Pat. No. 3,425,419 to Dato and U.S. Pat. No. 5,486,208 to Ginsburg disclose catheters for cooling the blood to create total body hypothermia However, they rely on circulating a cold fluid to produce cooling. This is unsuitable for selective organ hypothermia, because cooling of the entire catheter by the cold fluid on its way to the organ would ultimately result in non-selective, or total body, cooling.

Total body hypothermia to provide organ protection has a number of drawbacks. First, it creates cardiovascular problems, such as cardiac arrhythmias, reduced cardiac output, and increased systemic vascular resistance. These side effects can result in organ damage. These side effects are believed to be caused reflexively in response to the reduction in core body temperature. Second, total body hypothermia is difficult to administer. Immersing a patient in ice water clearly has its associated problems. Placement on cardiopulmonary bypass requires surgical intervention and specialists to operate the machine, and it is associated with a number of complications including bleeding and volume overload. Third, the time required to reduce the body temperature and the organ temperature is prolonged. Minimizing the time between injury and the onset of cooling has been shown to produce better clinical outcomes.

Some physicians have immersed the patient's head in ice to provide brain cooling. There are also cooling helmets, or head gear, to perform the same. This approach suffers from the problems of slow cool down and poor temperature control due to the temperature gradient that must be established externally to internally. It has also been shown that complications associated with total body cooling, such as arrhythmia and decreased cardiac output, can also be caused by cooling of the face and head only.

Selective organ hypothermia has been studied by Schwartz, et. al. Utilizing baboons, blood was circulated and cooled externally from the body via the femoral artery and returned to the body through the carotid artery. This study showed that the brain could be selectively cooled to temperatures of 20° C. without reducing the temperature of the entire body. Subsequently, cardiovascular complications associated total body hypothermia did not occur. However, external circulation of the blood for cooling is not a practical approach for the treatment of humans. The risks of infection, bleeding, and fluid imbalance are great. Also, at least two arterial vessels must be punctured and cannulated. Further, percutaneous cannulation of the carotid artery is very difficult and potentially fatal, due to the associated arterial wall trauma. Also, this method could not be used to cool organs such as the kidneys, where the renal arteries cannot be directly cannulated percutaneously.

Selective organ hypothermia has also been attempted by perfusing the organ with a cold solution, such as saline or perflourocarbons. This is commonly done to protect the heart during heart surgery and is referred to as cardioplegia. This procedure has a number of drawbacks, including limited time of administration due to excessive volume accumulation, cost and inconvenience of maintaining the perfusate, and lack of effectiveness due to temperature dilution from the blood. Temperature dilution by the blood is a particular problem in high blood flow organs such as the brain. For cardioplegia, the blood flow to the heart is minimized, and therefore this effect is minimized.

Intravascular, selective organ hypothermia, created by cooling the blood flowing into the organ, is the ideal method. First, because only the target organ is cooled, complications associated with total body hypothermia are avoided. Second, because the blood is cooled intravascularly, or in situ, problems associated with external circulation of blood are eliminated. Third, only a single puncture and arterial vessel cannulation is required, and it can be performed at an easily accessible artery such as the femoral, subclavian, or brachial. Fourth, cold perfusate solutions are not required, thus eliminating problems with excessive fluid accumulation. This also eliminates the time, cost, and handling issues associated with providing and maintaining cold perfusate solution. Fifth, rapid cooling can be achieved. Sixth, precise temperature control is possible.

Previous inventors have disclosed the circulation of a cold fluid to produce total body hypothermia, by placing a probe into a major vessel of the body. This approach is entirely unfeasible when considering selective organ hypothermia, as will be demonstrated below.

The important factor related to catheter development for selective organ hypothermia is the small size of the typical feeding artery, and the need to prevent a significant reduction in blood flow when the catheter is placed in the artery. A significant reduction in blood flow would result in ischemic organ damage. While the diameter of the major vessels of the body, such as the vena cava and aorta, are as large as 15 to 20 mm., the diameter of the feeding artery of an organ is typically only 4.0 to 8.0 mm. Thus, a catheter residing in one of these arteries cannot be much larger than 2.0 to 3.0 mm. in outside diameter. It is not practical to construct a selective organ hypothermia catheter of this small size using the circulation of cold water or other fluid. Using the brain as an example, this point will be illustrated.

The brain typically has a blood flow rate of approximately 500 to 750 cc/min. Two carotid arteries feed this blood supply to the brain. The internal carotid is a small diameter artery that branches off of the common carotid near the angle of the jaw. To cool the brain, it is important to place some of the cooling portion of the catheter into the internal carotid artery, so as to minimize cooling of the face via the external carotid, since face cooling can result in complications, as discussed above. It would be desirable to cool the blood in this artery down to 32° C., to achieve the desired cooling of the brain. To cool the blood in this artery by a 5° C. drop, from 37° C. down to 32° C., requires between 100 and 150 watts of refrigeration power.

In order to reach the internal carotid artery from a femoral insertion point, an overall catheter length of approximately 100 cm. would be required. To avoid undue blockage of the blood flow, the outside diameter of the catheter can not exceed approximately 2 mm. Assuming a coaxial construction, this limitation in diameter would dictate an internal supply tube of about 0.70 mm. diameter, with return flow being between the internal tube and the external tube.

A catheter based on the circulation of water or saline operates on the principle of transferring heat from the blood to raise the temperature of the water. Rather than absorbing heat by boiling at a constant temperature like a freon, water must warm up to absorb heat and produce cooling. Water flowing at the rate of 5.0 grams/sec, at an initial temperature of 0° C. and warming up to 5° C., can absorb 100 watts of heat. Thus, the outer surface of the heat transfer element could only be maintained at 5° C., instead of 0° C. This will require the heat transfer element to have a surface area of approximately 1225 mm$^2$. If a catheter of approximately 2.0 mm. diameter is assumed, the length of the heat transfer element would have to be approximately 20 cm.

In actuality, because of the overall length of the catheter, the water would undoubtedly warm up before it reached the heat transfer element, and provision of 0° C. water at the heat transfer element would be impossible. Circulating a cold liquid would cause cooling along the catheter body and could result in non-specific or total body hypothermia. Furthermore, to achieve this heat transfer rate, 5 grams/sec of water flow are required. To circulate water through a 100 cm. long, 0.70 mm. diameter supply tube at this rate produces a pressure drop of more than 3000 psi. This pressure exceeds the safety levels of many flexible medical grade plastic catheters. Further, it is doubtful whether a water pump that can generate these pressures and flow rates can be placed in an operating room.

BRIEF SUMMARY OF THE INVENTION

The selective organ cooling achieved by the present invention is accomplished by placing a cooling catheter into the feeding artery of the organ. The cooling catheter is based on the vaporization and expansion of a compressed and condensed refrigerant, such as freon. In the catheter, a shaft or body section would carry the liquid refrigerant to a distal heat transfer element where vaporization, expansion, and cooling would occur. Cooling of the catheter tip to temperatures above minus 2° C. results in cooling of the blood flowing into the organ located distally of the catheter tip, and subsequent cooling of the target organ. For example, the catheter could be placed into the internal carotid artery, to cool the brain. The size and location of this artery places significant demands on the size and flexibility of the catheter. Specifically, the outside diameter of the catheter must be minimized, so that the catheter can fit into the artery without compromising blood flow. An appropriate catheter for this application would have a flexible body of 70 to 100 cm. in length and 2.0 to 3.0 mm. in outside diameter.

It is important for the catheter to be flexible in order to successfully navigate the arterial path, and this is especially true of the distal end of the catheter. So, the distal end of the catheter must have a flexible heat transfer element, which is composed of a material which conducts heat better than the remainder of the catheter. The catheter body material could be nylon or PBAX, and the heat transfer element could be made from nitinol, which would have approximately 70 to 100 times the thermal conductivity of the catheter body material, and which is also superelastic. Nitinol could also be treated to undergo a transition to another shape, such as a coil, once it is placed in the proper artery. Certain tip shapes could improve heat transfer as well as allow the long tip to reside in arteries of shorter length.

The heat transfer element would require sufficient surface area to absorb 100 to 150 watts of heat. This could be accomplished with a 2 mm. diameter heat transfer tube, 15 to 18 cm. in length, with a surface temperature of 0° C. Fins can be added to increase the surface area, or to maintain the desired surface area while shortening the length.

The cooling would be provided by the vaporization and expansion of a liquid refrigerant, such as a freon, across an expansion element, such as a capillary tube. For example, freon R12 boiling at 1 atmosphere and a flow rate of between 0.11 and 0.18 liter/sec could provide between approximately 100 and 150 watts of refrigeration power. Utilizing a liquid refrigerant allows the cooling to be focused at the heat transfer element, thereby eliminating cooling along the catheter body. Utilizing boiling heat transfer to the expanded fluid also lowers the fluid flow rate requirement to remove the necessary amount of heat from the blood. This is important because the required small diameter of the catheter would have higher pressure drops at higher flow rates.

The catheter would be built in a coaxial construction with a 0.70 mm. inner supply tube diameter and a 2.0 mm. outer return tube diameter. This limits the pressure drops of the freon along the catheter length, as well as minimizing the catheter size to facilitate carotid placement. The inner tube would carry the liquid freon to the tubular heat transfer element at the distal end of the catheter body. If a heat transfer element surface temperature of 0° C. is maintained, just above the freezing point of blood, then 940 mm$^2$ of surface area in contact with the blood are required to lower the temperature of the blood by the specified 5° C. drop. This translates to a 2.0 mm. diameter heat transfer tube by 15 cm. in length. To generate 0° C. on the nitinol surface, the freon must boil at a temperature of minus 28° C. It is important to have boiling heat transfer, which has a higher heat transfer coefficient, to maintain the surface temperature at 0° C. There are several freons that can be controlled to boil at minus 28° C., such as a 50/50 mixture of pentafluoroethane and 1,1,1 trifluoroethane or a 50/50 mixture of difluoromethane and pentafluoroethane. The 50/50 mixture of pentafluoroethane and 1,1,1 trifluoroethane would require a flow rate of approximately 7.0 liters/min or 0.52 gram/sec to absorb 100 watts of heat. At this flow rate, the pressure drop along the inner tube is less than 7 psi in 100 cm. of length, and the pressure drop along the outer tube is less than 21 psi in 100 cm. of length.

The inner supply tube of the catheter would be connected to a condenser, fed by the high pressure side of a compressor, and the outer return tube of the catheter would be connected to the low pressure side of the compressor.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
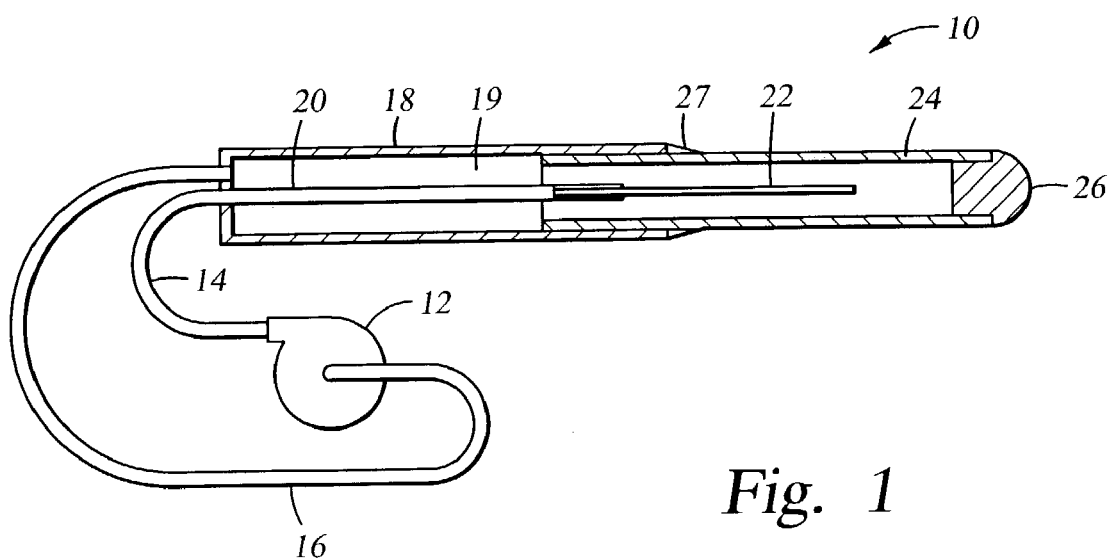
FIG. 1 is a schematic, partially in section, showing a first embodiment of the flexible catheter according to the present invention.

As shown in FIG. 1, the apparatus of the present invention includes a flexible catheter assembly 10, fed by a refrigeration compressor unit 12, which can include a condenser. The compressor unit 12 has an outlet 14 and an inlet 16. The catheter assembly 10 has an outer flexible catheter body 18, which can be made of braided PBAX or other suitable catheter material. The catheter body 18 must be flexible, to enable passage through the vascular system of the patient to the feeding artery of the selected organ. The inner lumen 19 of the catheter body 18 serves as the return flow path for the expanded refrigerant. The catheter assembly 10 also has an inner flexible refrigerant supply conduit 20, which can be made of nylon, polyimide, nitinol, or other suitable catheter material. The length and diameter of the catheter body 18 and refrigerant supply conduit 20 are designed for the size and location of the artery in which the apparatus will be used. For use in the internal carotid artery to achieve hypothermia of the brain, the catheter body 18 and refrigerant supply conduit 20 will have a length of approximately 70 to 100 centimeters. The catheter body 18 for this application will have an outside diameter of approximately 2.5 millimeters and an inside diameter of approximately 2.0 millimeters, and the refrigerant supply conduit will have an outside diameter of approximately 1.0 millimeter and an inside diameter of approximately 0.75 millimeter. A supply conduit 20 of this diameter will have a refrigerant pressure drop of only approximately 0.042 atmospheres per 100 centimeters. The return flow path through a catheter body 18 of this diameter will have a refrigerant pressure drop of only approximately 0.064 atmospheres per 100 centimeters.

The compressor outlet 14 is attached in fluid flow communication, by known means, to a proximal end of the refrigerant supply conduit 20 disposed coaxially within said catheter body 18. The distal end of the refrigerant supply conduit 20 is attached to an expansion element, which in this embodiment is a capillary tube 22 having a lenght of approximately 15 to 25 centimeters. The capillary tube 22 can be made of polyimide or nitinol, or other suitable material, and it can be a separate element attached to the supply conduit 20, or it can be an integral portion of the supply conduit 20. For the internal carotid artery application, the capillary tube 22 will have an outside diameter of approximately 0.6 millimeter and an inside diameter of approximately 0.25 millimeter. The expansion element, such as the capillary tube 22, has an outlet within a chamber of a flexible heat transfer element such as the hollow flexible tube 24. The tube 24 shown in this embodiment is flexible but essentially straight in its unflexed state. The heat transfer element must be flexible, to enable passage through the vascular system of the patient to the feeding artery of the selected organ. For the internal carotid application the flexible tube 24 will have a length of approximately 15 centimeters, an outside diameter of approximately 1.9 millimeters and an inside diameter of approximately 1.5 millimeters. The heat transfer element also includes a plug 26 in the distal end of the flexible tube 24. The plug 26 can be epoxy potting material, plastic, or a metal such as stainless steel or gold. A tapered transition of epoxy potting material can be provided between the catheter body 18 and the flexible tube 24.

A refrigerant, such as freon, is compressed, condensed, and pumped through the refrigerant supply conduit 20 to the expansion element, or capillary tube, 22. The refrigerant vaporizes and expands into the interior chamber of the heat transfer element, such as the flexible tube 24, thereby cooling the heat transfer element 24. Blood in the feeding artery flows around the heat transfer element 24, thereby being cooled. The blood then continues to flow distally into the selected organ, thereby cooling the organ.

Figure 2:
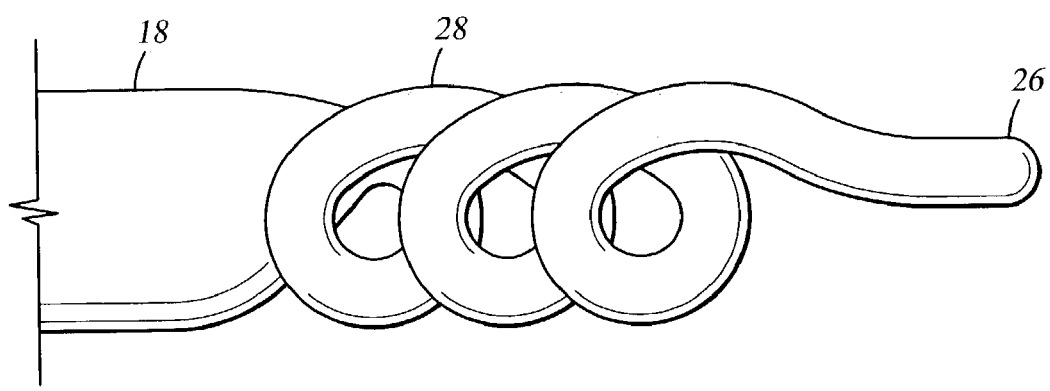
FIG. 2 is a perspective view of a second embodiment of the distal tip of the catheter of the present invention, after transformation.

A second embodiment of the heat transfer element is shown in FIG. 2. This embodiment can be constructed of a tubular material such as nitinol, which has a temperature dependent shape memory. The heat transfer element 28 can be originally shaped like the flexible tube 24 shown in FIG. 1, at room temperature, but trained to take on the coiled tubular shape shown in FIG. 2 at a lower temperature. This allows easier insertion of the catheter assembly 10 through the vascular system of the patient, with the essentially straight but flexible tubular shape, similar to the flexible tube 24. Then, when the heat transfer element is at the desired location in the feeding artery, such as the internal carotid artery, refrigerant flow is commenced. As the expanding refrigerant, such as a 50/50 mixture of pentafluoroethane and 1,1,1 trifluoroethane or a 50/50 mixture of difluoromethane and pentafluoroethane, cools the heat transfer element down, the heat transfer element takes on the shape of the heat transfer coil 28 shown in FIG. 2. This enhances the heat transfer capacity, while limiting the length of the heat transfer element.

Figure 3:
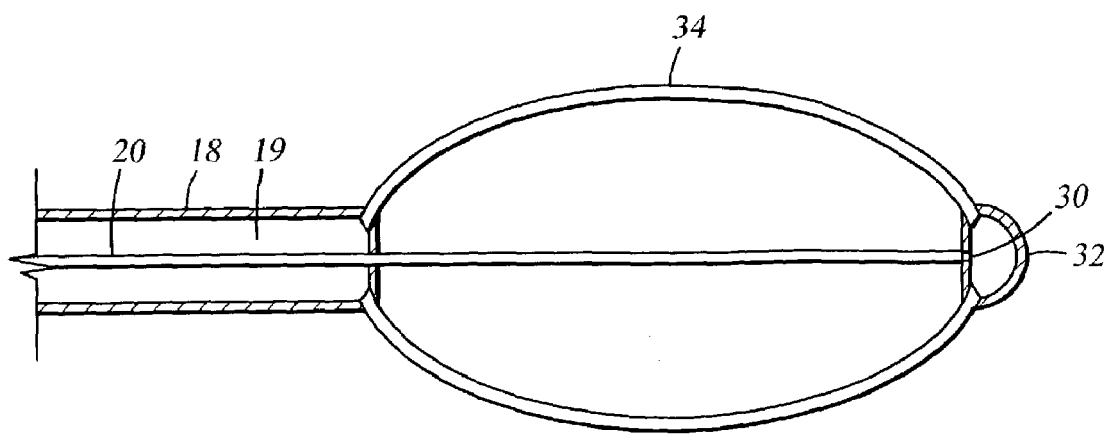
FIG. 3 is a section view of a third embodiment of the distal tip of the catheter of the present invention, after expansion of the heat transfer element.

A third embodiment of the expansion element and the heat transfer element is shown in FIG. 3. This embodiment of the expansion element is an orifice 30, shown at the distal end of the refrigerant supply conduit 20. The outlet of the orifice 30 discharges into an expansion chamber 32. In this embodiment, the heat transfer element is a plurality of hollow tubes 34 leading from the expansion chamber 32 to the refrigerant return lumen 19 of the catheter body 18. This embodiment of the heat transfer element 34 can be constructed of a tubular material such as nitinol, which has a temperature dependent shape memory, or some other tubular material having a permanent bias toward a curved shape. The heat transfer element tubes 34 can be essentially straight, originally, at room temperature, but trained to take on the outwardly flexed "basket" shape shown in FIG. 3 at a lower temperature. This allows easier insertion of the catheter assembly 10 through the vascular system of the patient, with the essentially straight but flexible tubes. Then, when the heat transfer element 34 is at the desired location in the feeding artery, such as the internal carotid artery, refrigerant flow is commenced. As the expanding refrigerant cools the heat transfer element 34 down, the heat transfer element takes on the basket shape shown in FIG. 3. This enhances the heat transfer capacity, while limiting the length of the heat transfer element.

Figure 4:
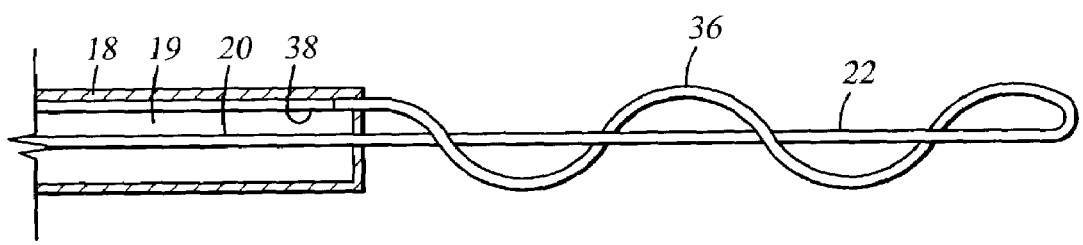
FIG. 4 is a partial section view of a fourth embodiment of the distal tip of the catheter of the present invention, after transformation.

A fourth embodiment of the heat transfer element is shown in FIG. 4. This embodiment can be constructed of a material such as nitinol. The heat transfer element 36 can be originally shaped as a long loop extending from the distal end of the catheter body 18, at room temperature, but trained to take on the coiled tubular shape shown in FIG. 4 at a lower temperature, with the heat transfer element 36 coiled around the capillary tube 22. This allows easier insertion of the catheter assembly 10 through the vascular system of the patient, with the essentially straight but flexible tubular loop shape. Then, when the heat transfer element 36 is at the desired location in the feeding artery, such as the internal carotid artery, refrigerant flow is commenced. As the expanding refrigerant cools the heat transfer element down, the heat transfer element takes on the shape of the coil 36 shown in FIG. 4. This enhances the heat transfer capacity, while limiting the length of the heat transfer element 36. FIG. 4 further illustrates that a thermocouple 38 can be incorporated into the catheter body 18 for temperature sensing purposes.

Figure 5:
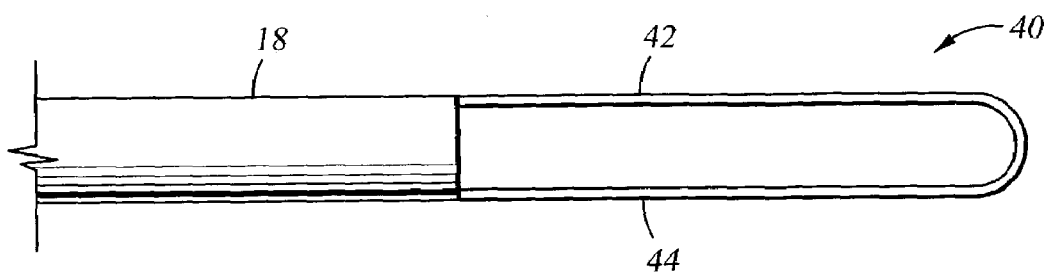
FIG. 5 is an elevation view of a fifth embodiment of the distal tip of the catheter of the present invention, before transformation.
Figure 6:
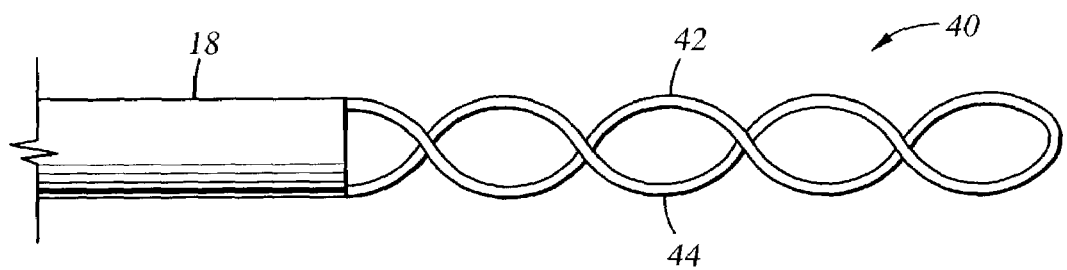
FIG. 6 is an elevation view of the embodiment shown in FIG. 5, after transformation to a double helix.
Figure 7:
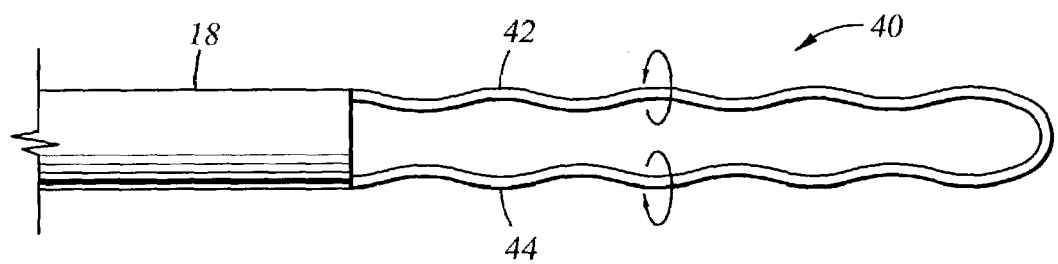
FIG. 7 is an elevation view of the embodiment shown in FIG. 5, after transformation to a looped coil.

Yet a fifth embodiment of the heat transfer element is shown in FIGS. 5, 6, and 7. In this embodiment, an expansion element, such as a capillary tube or orifice, is incorporated within the distal end of the catheter body 18. This embodiment of the heat transfer element can be constructed of a material such as nitinol. The heat transfer element is originally shaped as a long loop 40 extending from the distal end of the catheter body 18, at room temperature. The long loop 40 has two sides 42, 44, which are substantially straight but flexible at room temperature. The sides 42, 44 of the long loop 40 can be trained to take on the double helical shape shown in FIG. 6 at a lower temperature, with the two sides 42, 44 of the heat transfer element 40 coiled around each other. Alternatively, the sides 42, 44 of the long loop 40 can be trained to take on the looped coil shape shown in FIG. 7 at a lower temperature, with each of the two sides 42, 44 of the heat transfer element 40 coiled independently. Either of these shapes allows easy insertion of the catheter assembly 10 through the vascular system of the patient, with the essentially straight but flexible tubular loop shape. Then, when the heat transfer element 40 is at the desired location in the feeding artery, such as the internal carotid artery, refrigerant flow is commenced. As the expanding refrigerant cools the heat transfer element down, the heat transfer element 40 takes on the double helical shape shown in FIG. 6 or the looped coil shape shown in FIG. 7. Both of these configurations enhance the heat transfer capacity, while limiting the length of the heat transfer element 40.

Figure 8:
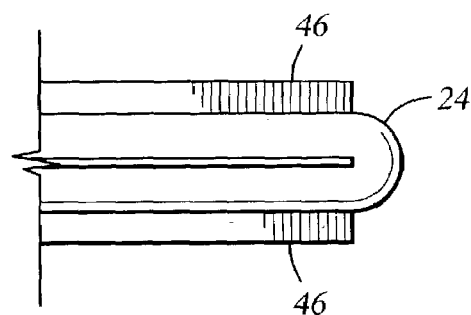
FIG. 8 is an elevation view of a sixth embodiment of the distal tip of the catheter of the present invention, showing longitudinal fins on the heat transfer element.
Figure 9:
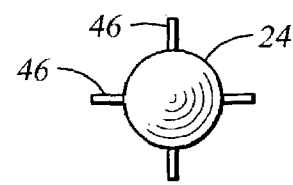
FIG. 9 is an end view of the embodiment shown in FIG. 8.

As shown in FIGS. 8 through 11, the heat transfer element 24 can have external fins 46, 48 attached thereto, such as by welding or brazing, to promote heat transfer. Use of such fins allows the use of a shorter heat transfer element without reducing the heat transfer surface area, or increases the heat transfer surface area for a given length. In FIGS. 8 and 9, a plurality of longitudinal fins 46 are attached to the heat transfer element 24. The heat transfer element 24 in such an embodiment can have a diameter of approximately 1.0 millimeter, while each of the fins 46 can have a width of approximately 0.5 millimeter and a thickness of approximately 0.12 millimeter. This will give the heat transfer element an overall diameter of approximately 2.0 millimeters, still allowing the catheter to be inserted into the internal carotid artery.

Figure 10:
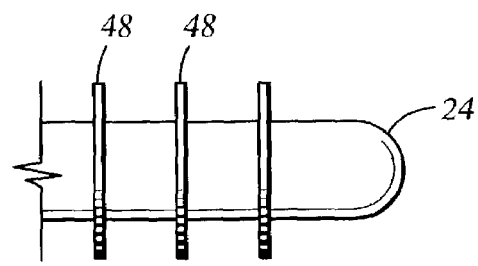
FIG. 10 is an elevation view of a seventh embodiment of the distal tip of the catheter of the present invention, showing annular fins on the heat transfer element.
Figure 11:
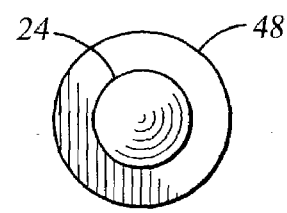
FIG. 11 is an end view of the embodiment shown in FIG. 10.

In FIGS. 10 and 11, a plurality of annular fins 48 are attached to the heat transfer element 24. The heat transfer element 24 in such an embodiment can have a diameter of approximately 1.0 millimeter, while each of the fins 48 can have a width of approximately 0.5 millimeter and a thickness of approximately 0.12 millimeter. This will give the heat transfer element an overall diameter of approximately 2.0 millimeters, still allowing the catheter to be inserted into the internal carotid artery.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

What is claimed is:

1. A method for treating an effect of disruption of blood flow to an organ using hypothermia, comprising:
   resuscitating the patient; and
   inducing hypothermia in the patient, wherein hypothermia is induced by circulating a heat exchange fluid through a catheter, having a flexible heat transfer element disposed at a distal portion thereof, positioned in the patient's central venous system,
   wherein the flexible heat transfer element is flexible enough to navigate from a femoral insertion point to at least a common carotid artery.

2. A method for treating an effect of disruption of blood flow to an organ using hypothermia, comprising:
   inducing hypothermia in the patient, wherein hypothermia is induced by circulating a heat exchange fluid through a flexible catheter, having a flexible heat transfer element disposed at a distal portion thereof, positioned in the patient's central venous system,
   wherein the flexible heat transfer element is flexible enough to navigate from a femoral insertion point to at least a common carotid artery.

3. A method for treating an effect of disruption of blood flow to an organ using hypothermia, comprising:
   percutaneously inserting a flexible catheter into a patient's central venous system; and inducing hypothermia in the patient, wherein hypothermia is induced by circulating a heat exchange fluid through the flexible catheter, having a flexible heat transfer element disposed at a distal portion thereof, positioned in the patient's central venous system, wherein the flexible heat transfer element is flexible enough to navigate from a femoral insertion point to at least a common carotid artery.

4. A method for treating an effect of disruption of blood flow to the heart using hypothermia, comprising:

percutaneously inserting a flexible catheter into a patient's central venous system;

inducing hypothermia in the patient, wherein hypothermia is induced by circulating a heat exchange fluid through the flexible catheter, having a flexible heat transfer element disposed at a distal portion thereof, positioned in the patient's central venous system, wherein the flexible heat transfer element is flexible enough to navigate from a femoral insertion point to at least a common carotid artery.

5. A method for treating an effect of disruption of blood flow to the brain using hypothermia, comprising:

percutaneously inserting a flexible catheter into a patient's central venous system;

inducing hypothermia in the patient, wherein hypothermia is induced by circulating a heat exchange fluid through the flexible catheter, having a flexible heat transfer element disposed at a distal portion thereof, positioned in the patient's central venous system, wherein the flexible heat transfer element is flexible enough to navigate from a femoral insertion point to at least a common carotid artery.

* * * * *